(12) United States Patent
Yoshida

(10) Patent No.: US 8,953,742 B2
(45) Date of Patent: Feb. 10, 2015

(54) RADIATION IMAGE DETECTING DEVICE AND METHOD FOR CONTROLLING THE SAME

(75) Inventor: Yutaka Yoshida, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 471 days.

(21) Appl. No.: 13/290,750

(22) Filed: Nov. 7, 2011

(65) Prior Publication Data
US 2012/0114099 A1    May 10, 2012

(30) Foreign Application Priority Data
Nov. 9, 2010  (JP) .................................. 2010-250727

(51) Int. Cl.
*G01N 23/04* (2006.01)
*A61B 6/00* (2006.01)

(52) U.S. Cl.
CPC .............. *A61B 6/4233* (2013.01); *A61B 6/4283* (2013.01); *A61B 6/541* (2013.01); *A61B 6/4021* (2013.01)
USPC ........................................... 378/62; 378/114

(58) Field of Classification Search
CPC ....................................................... A61B 6/542
USPC ........................................... 378/114–116, 62
See application file for complete search history.

(56) References Cited

U.S. PATENT DOCUMENTS

| | | | |
|---|---|---|---|
| 6,797,960 | B1 | 9/2004 | Spartiotis et al. |
| 2002/0001366 | A1* | 1/2002 | Tamura et al. .................. 378/155 |
| 2003/0081823 | A1 | 5/2003 | Nonaka |
| 2003/0086523 | A1 | 5/2003 | Tashiro et al. |
| 2010/0054405 | A1 | 3/2010 | Taoka et al. |

FOREIGN PATENT DOCUMENTS

| | | |
|---|---|---|
| EP | 1 139 118 A2 | 10/2001 |
| JP | 2002-272711 A | 9/2002 |

(Continued)

OTHER PUBLICATIONS

Notification of Reasons for Refusal, dated Oct. 24, 2012, issued in corresponding JP Application No. 2010-250727, 5 pages in English and Japanese.

(Continued)

*Primary Examiner* — Hoon Song
(74) *Attorney, Agent, or Firm* — Sughrue Mion, PLLC

(57) ABSTRACT

An acceleration sensor is installed in an electronic cassette. The acceleration sensor detects a shake. When magnitude of the shake, measured using the acceleration sensor, is greater than or equal to a shake detection threshold value, a judging circuit of a shake detecting section turns off a switching element. An operation switching section is disconnected from an irradiation detecting section that detects a start of X-ray irradiation. Thus, an irradiation detection function of the irradiation detecting section is disabled. After a predetermined time, the judging circuit outputs an ON signal to the switching element to turn on the switching element. Thereby, the irradiation detecting section resumes the irradiation detection.

13 Claims, 7 Drawing Sheets

(56) References Cited

FOREIGN PATENT DOCUMENTS

| | | | |
|---|---|---|---|
| JP | 2002-543684 | A | 12/2002 |
| JP | 2003-126072 | A | 5/2003 |
| JP | 2006-246961 | A | 9/2006 |
| JP | 2008-125903 | A | 6/2008 |
| JP | 2008-132216 | A | 6/2008 |
| JP | 2009-195612 | A | 9/2009 |
| JP | 2009-201561 | A | 9/2009 |
| JP | 2010-121944 | A | 6/2010 |

OTHER PUBLICATIONS

Communication, dated Mar. 20, 2012, issued in corresponding EP Application No. 11188075.3, 7 pages.

Decision of Refusal, dated Jan. 16, 2013, issued in corresponding JP Application No. 2010-250727, 5 pages in English and Japanese.

The First Office Action, dated Oct. 16, 2014, issued in corresponding CN Application No. 201110353444.X, 15 pages in English and Chinese.

* cited by examiner

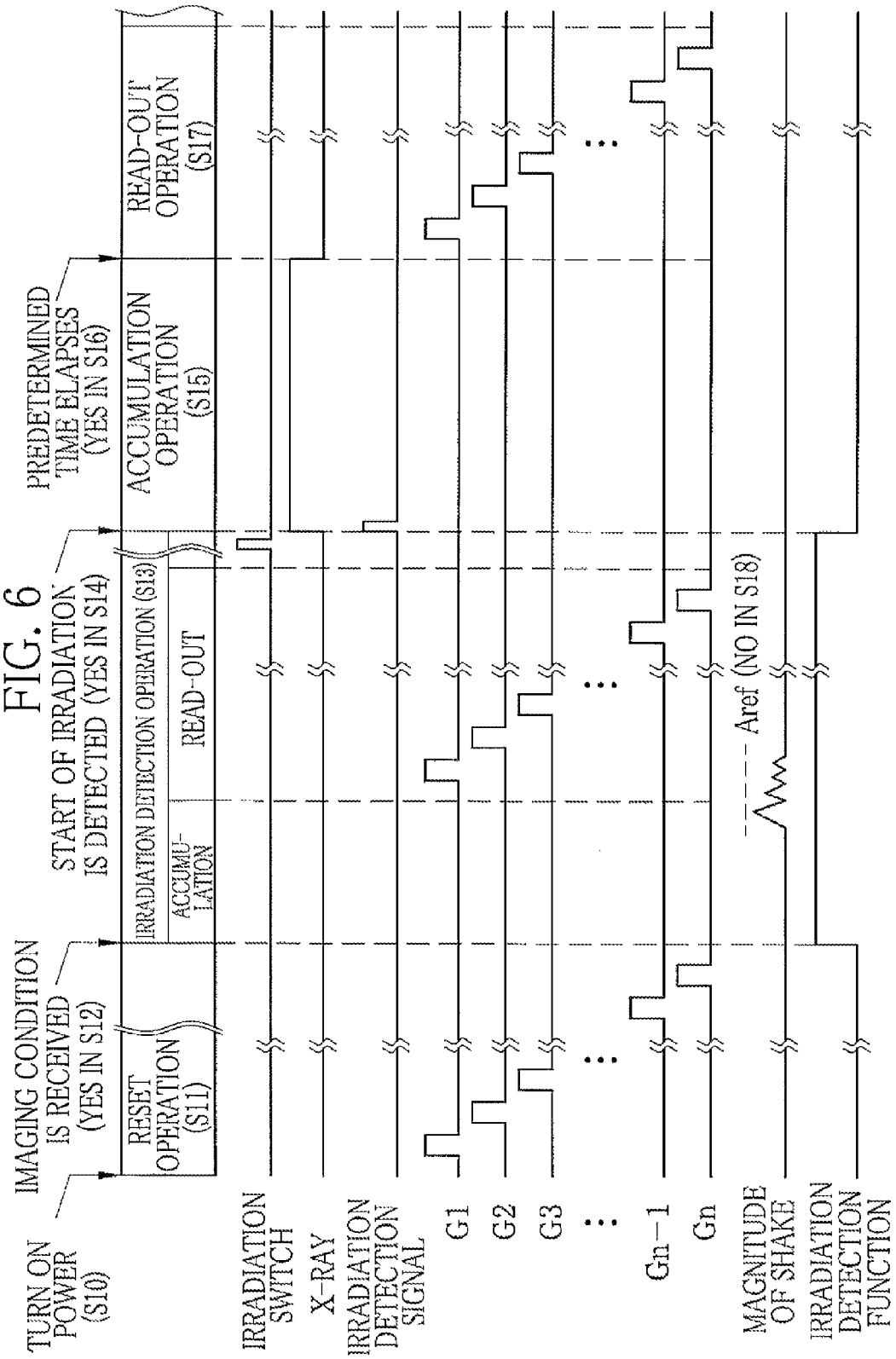

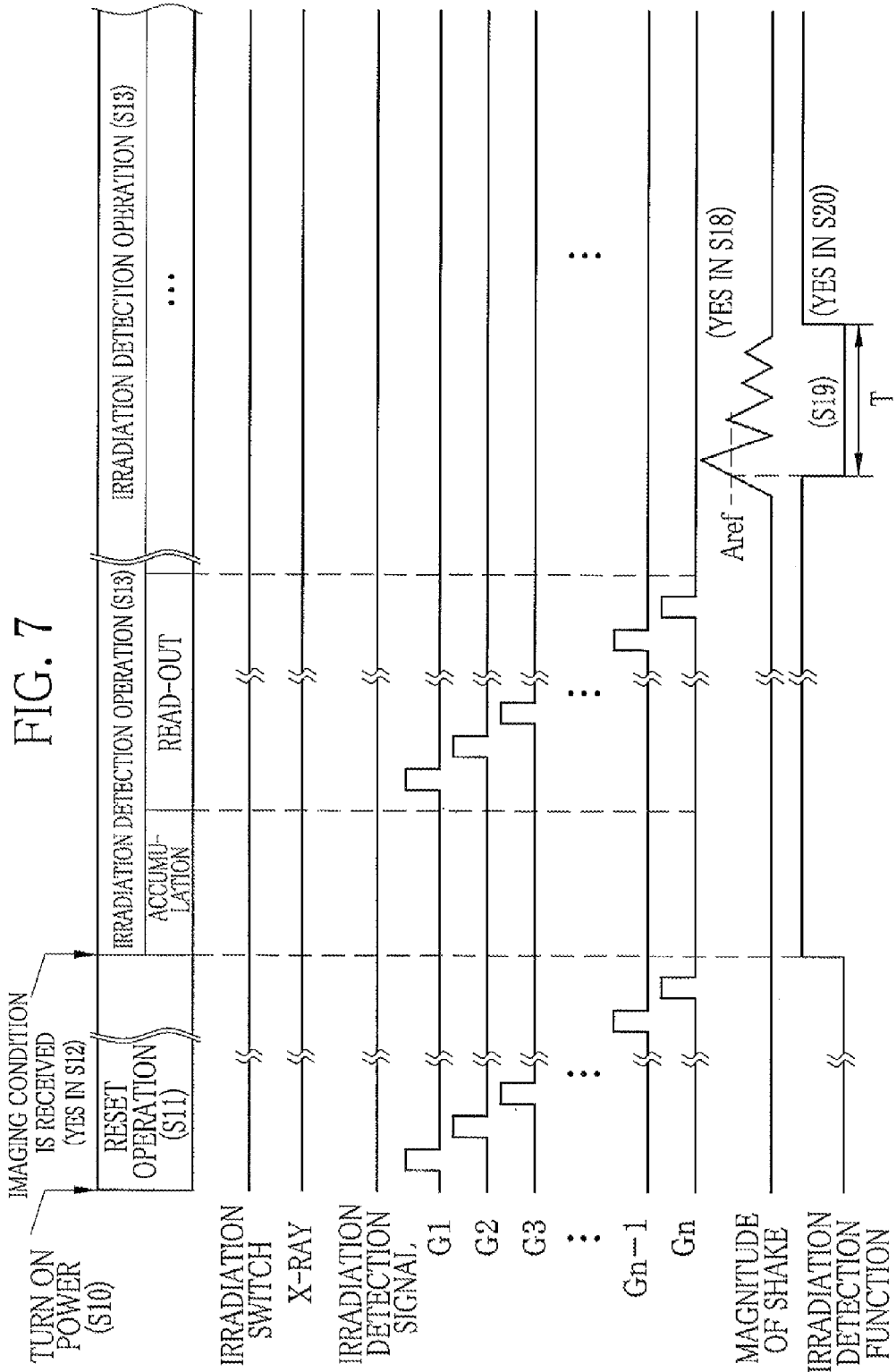

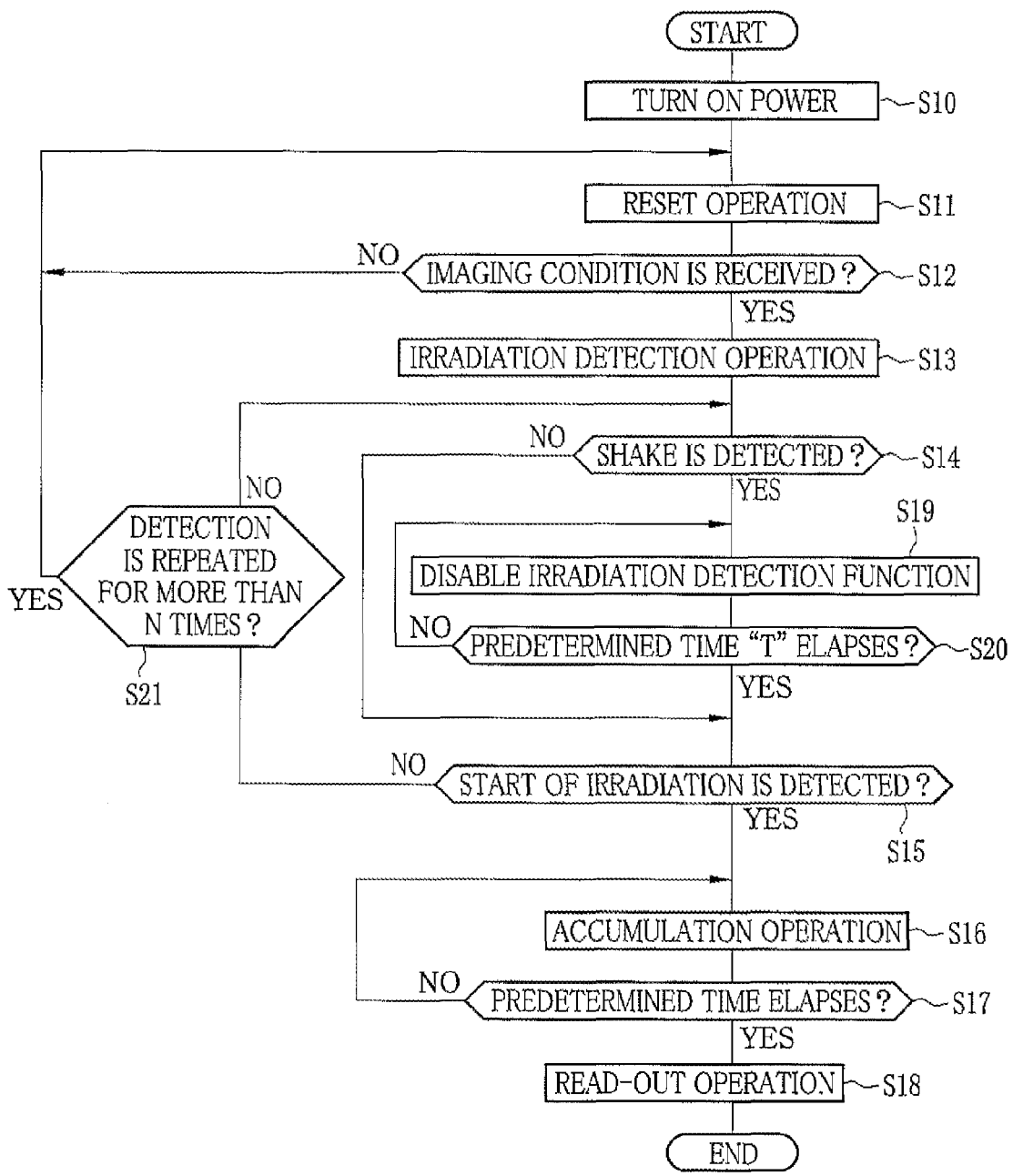

RADIATION IMAGE DETECTING DEVICE AND METHOD FOR CONTROLLING THE SAME

BACKGROUND OF THE INVENTION

1. Field of the Invention

The present invention is related to a radiation image detection device for use in a radiation imaging system and a method for controlling the same.

2. Description Related to the Prior Art

A radiation imaging system, for example, an X-ray imaging system is composed of an X-ray generating apparatus and an X-ray imaging apparatus. The X-ray generating apparatus generates X-rays. The X-ray imaging apparatus captures an X-ray image formed by the X-rays passed through a subject. The X-ray generating apparatus has an X-ray source, a source control device, and an irradiation switch, for example. The X-ray source emits the X-rays to a subject (a patient). The source control device controls the X-ray source. The irradiation switch is used for inputting a command to start X-ray irradiation. The X-ray imaging apparatus has an X-ray image detection device and an imaging control device. The X-ray image detection device detects the X-ray image based on the X-rays passed through the subject. The imaging control device controls the X-ray image detection device.

For the X-ray image detection device, recently, a flat panel detector (FPD) has been commonly used as an X-ray image detector instead of an X-ray film or an imaging plate (IP). The FPD has pixels arranged in a matrix. Each pixel accumulates signal charge in accordance with an amount of the incident X-rays. By accumulating the signal charge on a pixel-by-pixel basis, the FPD detects an X-ray image representing image information of the subject. Then, the FPD outputs the X-ray image as digital image data.

A portable X-ray image detection device (hereinafter referred to as the electronic cassette) has also been put to practical use. The electronic cassette has the FPD enclosed in a rectangular solid housing. The electronic cassette may be attached to an imaging bed or platform originally designed for a film cassette or an IP cassette. Alternatively, for example, when it is difficult to capture an image of a region of interest using a stationary imaging system because of the location of the region of interest, the patient himself or herself may hold the electronic cassette when the X-ray imaging is performed. The electronic cassette may be used on-site (outside of a hospital) without the use of the imaging bed, to perform X-ray imaging of a patient requiring emergency medical care in, for example, an accident or disaster scene or of an elderly patient requiring home care.

Conventionally, to synchronize the X-ray irradiation caused by pressing of the irradiation switch and the start of the accumulation operation of the signal charge by the X-ray image detection device, the source control device of the X-ray generating apparatus and the imaging control device of the X-ray imaging apparatus exchange an operation signal, being a synchronization signal representing the start of the X-ray irradiation, issued by the irradiation switch. In this case, the X-ray generating apparatus and the X-ray imaging apparatus need to be connected to each other electrically. However, if the X-ray generating apparatus and the X-ray imaging apparatus are produced by different manufacturers and their connection interfaces (for example, standards of cables, connectors, and formats of the synchronization signals) are not compatible with each other, a new interface needs to be provided.

To solve the problem, it is suggested that the X-ray image detection device itself detects the start of the irradiation of the X-rays to synchronize with the X-ray generating apparatus without exchanging the synchronization signal (without the electrical connection) between the X-ray image detection device and the X-ray generating apparatus (see U.S. Patent Application Publication No. 2003/0086523 corresponding to Japanese Patent Laid-Open Publication No. 2003-126072, U.S. Pat. No. 6,797,960 corresponding to Japanese translation of PCT International Publication No. 2002-543684, and U.S. Patent Application Publication No. 2010/0054405 corresponding to Japanese Patent Laid-Open Publication No. 2008-125903).

In the U.S. Patent Application Publication No. 2003/0086523, the X-ray image detection device performs the read-out operation (nondestructive read-out) of the signal charge at a predetermined frame rate. A difference between an image of the present frame outputted by the read-out operation and an image of the previous frame is obtained. The difference is compared with a threshold value. When the difference exceeds the threshold value, it is detected or judged that the X-ray irradiation has been started. In the U.S. Pat. No. 6,797,960, the bias current of the FPD is detected. The bias current is an output value from an area of the FPD where the X-rays are incident without passing through a subject. A differential value of the bias current is compared with a threshold value to detect or judge the start of the X-ray irradiation. In the U.S. Patent Application Publication No. 2010/0054405, the X-ray image detection device is provided with a photodiode for detecting the X-rays. A reference signal generated based on an offset value of the photodiode is compared with an output signal from the photodiode. When the output signal value exceeds the reference signal value, it is determined that the X-ray irradiation has been started.

Generally, an output from an electrical component is affected by noise caused by an internal factor of the component itself or an external factor such as ambient environment. The X-ray image detection device composed of a plurality of electrical components is no exception. For example, when a subject or radiological technologist bumps into the X-ray image detection device inadvertently, vibration or shake caused by the impact causes noise. False detection of the X-ray irradiation occurs if the noise affects a signal for detecting the start of the X-ray irradiation, though the X-ray irradiation has not been started actually. Power consumption increases when the false detection induces unnecessary operations of the X-ray image detection device. Because the X-ray imaging cannot be performed during the irradiation detection operation, an operator is likely to miss the timing for shooting.

Moreover, the imaging control device and a device (for example, a console) for setting imaging conditions, both connected to the X-ray image detection device, may go through unnecessary operations as if the image capture has been performed. Accordingly, burdensome operations such as resetting the imaging conditions are necessary. Even if the start of the X-ray irradiation is detected or judged erroneously, it may be handled as if the X-ray imaging is performed appropriately. An image resulting from the false detection may be transmitted as a correct image to a doctor. This may cause medical malpractice.

In the U.S. Patent Application Publication No. 2003/0086523, a difference between the image of the present frame and the image of the previous frame is compared with the threshold value. Noise is added only to the present frame, and thereby the image signal exceeds the threshold value. As a result, the false detection occurs. In the method of the U.S.

Pat. No. 6,797,960, there is a possibility of the false detection when the bias current varies due to noise. Similarly, in the method of the U.S. Patent Application Publication No. 2010/0054405, the false detection occurs when a noise component greater than or equal to the reference signal is added to the output from the photodiode.

All of the methods described in the U.S. Patent Application Publication No. 2003/0086523, the U.S. Pat. No. 6,797,960, and the U.S. Patent Application Publication No. 2010/0054405 are susceptible to noise, so these methods are at increased risk of erroneously detecting the start of the X-ray irradiation.

However, none of the above describes how to prevent the false detection caused by noise.

SUMMARY OF THE INVENTION

An object of the present invention is to provide a radiation image detection device for surely preventing false detection of a start of radiation irradiation and a method for controlling a radiation image detection device.

A radiation image detection device of the present invention includes a radiation image detector, an irradiation sensor, an irradiation detecting section, a noise sensor, and a control section. The radiation image detector has a plurality of pixels arranged thereon. The radiation image detector performs accumulation operation in which each pixel detects radiation, emitted from a radiation source, to accumulate signal charge. The irradiation sensor detects the radiation. The irradiation detecting section detects a start of irradiation of the radiation based on a signal from the irradiation sensor. The control section enables or disables the irradiation detecting section based on a signal from the noise sensor.

It is preferable that the control section includes a noise detecting section for detecting magnitude of the signal from the noise sensor. The noise detecting section outputs a first signal to the control section when the magnitude of the signal from the noise sensor is greater than or equal to a first threshold value. The control section disables the irradiation detecting section when the first signal is inputted from the noise detecting section.

It is preferable that the irradiation detecting section outputs a second signal to the control section when magnitude of the signal from the irradiation sensor is greater than or equal to a second threshold value. The second signal represents the start of the irradiation of the radiation. The control section enables the irradiation detecting section to allow the radiation image detector to perform the accumulation operation when the second signal is inputted to the control section from the irradiation detecting section and the first signal is not inputted to the control section from the noise detecting section.

It is preferable that the control section disables the irradiation detecting section by disconnecting the control section from the irradiation detecting section.

It is preferable that the control section disables the irradiation detecting section by controlling the irradiation detecting section not to output the second signal.

It is preferable that the control section disables the irradiation detecting section by not receiving the second signal even if the second signal is inputted to the control section.

It is preferable that the control section disables the irradiation detecting section for a predetermined time after the first signal is outputted from the noise detecting section.

It is preferable that the predetermined time is a time necessary for a noise component in the signal from the irradiation sensor to decrease its magnitude to a negligible value.

It is preferable that the noise sensor is a vibration sensor and indirectly detects the noise from the magnitude of the vibration. It is preferable that the vibration sensor is an acceleration sensor.

It is preferable that the irradiation sensor also serves as the radiation image detector. In this case, it is preferable that the at least one pixel positioned close to a center of the radiation image detector is used as the irradiation sensor.

It is preferable that the control section allows the radiation image detector to perform an irradiation detection operation. The irradiation detection operation includes the accumulation operation and a read-out operation repeated alternately for the predetermined number of times. The signal charge is converted into an electric signal and then the electric signal is outputted in the read-out operation.

It is preferable that the radiation image detection device is an electronic cassette having the radiation image detector enclosed in a portable housing.

A method for controlling a radiation image detection device of the present invention includes a detecting step and a disabling step. In the detecting step, occurrence of a cause of noise is detected based on a signal from a noise sensor. In the disabling step, an irradiation detecting section is disabled when the signal is greater than or equal to a threshold value. The irradiation detecting section judges a start of irradiation of radiation based on a detection result of an irradiation sensor.

In the present invention, the irradiation detecting section is disabled when the noise greater than or equal to a predetermined value, which induces false detection of the start of the irradiation of radiation, is detected directly or indirectly. Accordingly, the false detection of the start of the radiation emission is surely prevented.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 6 is a timing chart showing a state where the irradiation detecting section is enabled;

FIG. 7 is a timing chart showing a state where the irradiation detecting section is disabled; and FIG. 8 is a flowchart showing an operation procedure of the electronic cassette.

DESCRIPTION OF THE PREFERRED EMBODIMENTS

Figure 1:
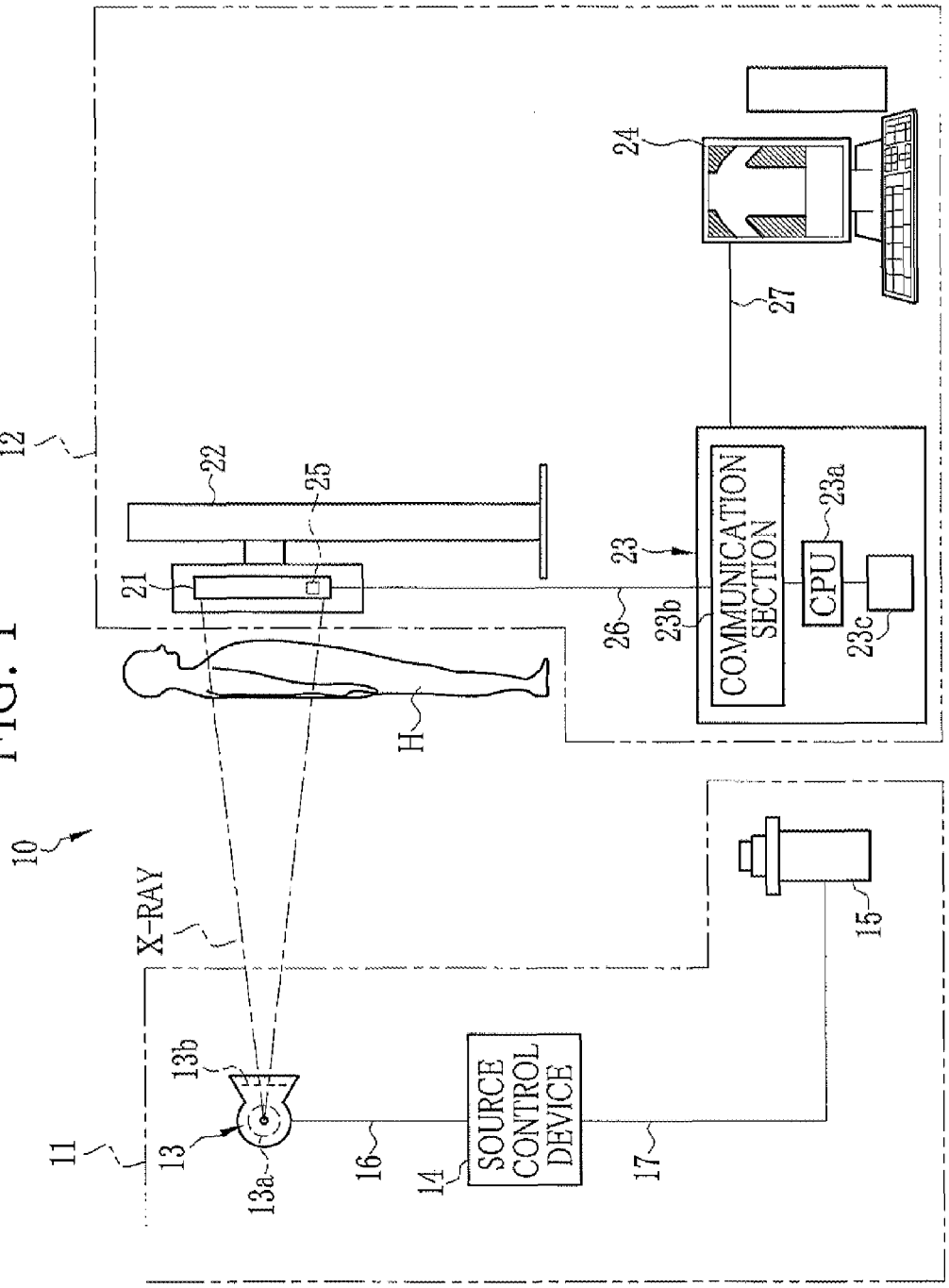
FIG. 1 is a schematic view of an X-ray imaging apparatus.

In FIG. 1, an X-ray imaging system 10 includes an X-ray generating apparatus 11 and an X-ray imaging apparatus 12. The X-ray generating apparatus 11 includes an X-ray source 13, a source control device 14 for controlling the X-ray source 13, and an irradiation switch 15. The X-ray source 13 has an X-ray tube 13a for emitting X-rays and a collimator 13b that limits an X-ray field of the X-rays emitted from the X-ray tube 13a.

The X-ray tube 13a includes a cathode and an anode (target). The cathode includes a filament for releasing thermoelectrons. When the thermoelectrons hit the target, X-rays are generated. The target is a rotating anode having a disc-shape. The target is rotated such that the focal spot moves along a circular path to disperse heat caused by the impact of the thermoelectrons. The collimator 13b has a plurality of lead plates for shielding the X-rays. The lead plates are arranged in parallel crosses with an irradiation opening formed at its center. The irradiation opening allows the X-rays to pass therethrough. Changing the positions of the lead plates varies the size of the irradiation opening to limit the X-ray field.

The source control device 14 includes a high voltage generator and a controller (both not shown). The high voltage generator supplies high voltage to the X-ray source 13. The controller controls tube voltage, tube current and X-ray irradiation time. The tube voltage determines energy spectrum of the X-rays emitted from the X-ray source 13. The tube current determines an amount of the X-rays emitted per unit time. The high voltage generator boosts the input voltage using a transformer to generate high tube voltage. Thereby, the high voltage generator supplies power to the X-ray source 13 via a high voltage cable 16. The X-ray generating apparatus 11 of this embodiment does not have a function to communicate with the X-ray imaging apparatus 12. The imaging conditions such as the tube voltage, the tube current, and the X-ray irradiation time are set manually via an operation panel of the source control device 14.

The irradiation switch 15 is connected to the source control device 14 via a signal cable 17. The irradiation switch 15 is a two-step push switch. When pressed one step, the irradiation switch generates a warm-up start signal for starting warm-up of the X-ray source 13. When pressed two steps down, the irradiation switch generates an irradiation start signal for allowing the X-ray source 13 to start the X-ray irradiation. These signals are inputted to the source control device 14 via the signal cable 17.

The source control device 14 controls the operation of the X-ray source 13 based on the signals from the irradiation switch 15. When the source control device 14 receives the warm-up start signal, the source control device 14 activates a heater (not shown) to preheat the filament. The source control device 14 also starts rotation of the target and allows the target to reach a predetermined speed of rotation. The warm-up time is in the order of approximately 200 milliseconds (msec) to 1500 msec. After an interval of the warm-up time after the irradiation switch 15 is pressed one step to instruct the start of the warm-up, the irradiation switch 15 is pressed two steps down to instruct the start of the irradiation.

Upon receipt of the irradiation start signal, the source control device 14 starts to supply the power to the X-ray source 13. The source control device 14 starts a timer to measure the X-ray irradiation time set according to the imaging conditions. When the X-ray irradiation time has elapsed, the source control device 14 causes the X-ray source 13 to stop the X-ray irradiation. The X-ray irradiation time varies according to the imaging conditions. In a still image capture setting, the maximum X-ray irradiation time is usually in a range from approximately 500 msec to approximately 2 seconds (sec). In setting the X-ray irradiation time, the maximum X-ray irradiation time is an upper limit.

The X-ray imaging apparatus 12 includes an electronic cassette 21, a support 22, an imaging control device 23, and a console 24. The electronic cassette 21 includes an acceleration sensor 25, an FPD 36 (see FIG. 2) being a radiation image detector, and a portable housing (not shown). The portable housing accommodates the acceleration sensor 25 and the FPD 36. The electronic cassette 21 converts the X-rays, emitted from the X-ray source 13 and passed through a subject (patient) H, into an X-ray image. The electronic cassette 21 has a flat plate-like shape with a rectangular plane. The size of the rectangular plane of the electronic cassette 21 is substantially the same as that of a film cassette or an IP cassette. The acceleration sensor 25 is used as a vibration sensor for detecting a shake or vibration of the electronic cassette 21. Noise is added to the X-ray detection signal in accordance with the magnitude of the shake. Here, the noise is detected indirectly from the shake of the electronic cassette 21.

The support 22 has a slot to which the electronic cassette 21 is attached in a removable manner. The support 22 supports the electronic cassette 21 such that an X-ray incidence surface of the electronic cassette 21 faces the X-ray source 13. Because the housing of the electronic cassette 21 has substantially the same size as the film cassette or the IP cassette, the electronic cassette 21 can be attached to a support for the film cassette or the IP cassette. The support 22 is a standing-position support that allows imaging of the patient H in a standing position by way of example. The support 22 may be a lying-position support that allows the imaging of the patient H in a lying position.

Figure 2:
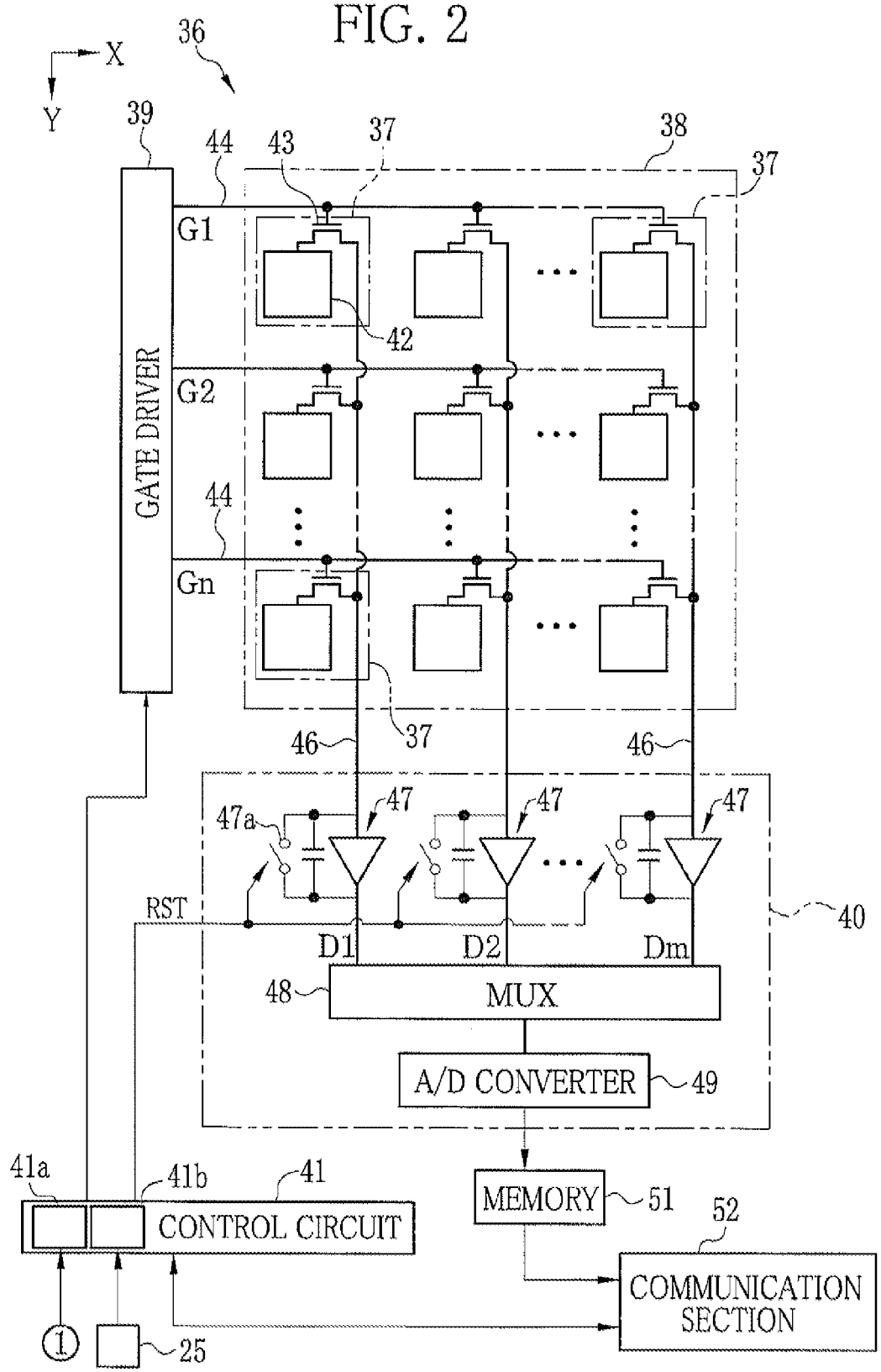
FIG. 2 is a block diagram showing an electrical configuration of an FPD.

In FIG. 2, the FPD 36 has a TFT active matrix substrate. The FPD 36 includes an imaging area 38, a gate driver 39, a signal processing circuit 40, and a control circuit 41. The imaging area 38 has a plurality of pixels 37 arranged on the TFT active matrix substrate. Each pixel accumulates signal charge in accordance with an amount of incident X-rays. The gate driver 39 drives the pixels 37 to control the read-out of the signal charge. The signal processing circuit 40 converts the signal charge read out from the pixels 37 into digital data, and outputs the digital data. The control circuit 41 controls the operation of the FPD 36 by operating the gate driver 39 and the signal processing circuit 40. The pixels 37 are arranged at a predetermined pitch in a two-dimensional matrix with n rows (in x direction) and m columns (in y direction).

The FPD 36 is an indirect conversion type detector. The FPD 36 has a scintillator (fluorescent substance or phosphor) that converts the X-rays into visible light. Then, the pixels 37 photoelectrically convert the visible light into electric charge. The scintillator is positioned to face the entire imaging area 38 where the pixels 37 are arranged. Alternatively, a direct conversion type FPD may be used. The direct conversion type FPD may use a conversion layer (for example, amorphous selenium) that converts the X-rays into electric charge directly.

Each pixel 37 is provided with a photodiode 42, a capacitor (not shown), and a thin film transistor (TFT) 43 being a switching element. The photodiode 42 is a photoelectric conversion element that generates electric charge (electron-hole pair) upon incidence of the visible light. The capacitor accumulates the electric charge generated by the photodiode 42.

The photodiode 42 has a semiconductor layer (for example, a PIN type) sandwiched between an upper electrode and a lower electrode. The semiconductor layer generates the electric charge. The TFT 43 is connected to the lower electrode. A bias line (not shown) is connected to the upper electrode. A bias voltage is applied to the upper electrode through the bias line. The application of the bias voltage generates an electric field in the semiconductor layer. The negative electrons are attracted to one of the upper and lower electrodes of positive polarity, and the positive holes are attracted to the other of negative polarity. Thus, the electric charge is accumulated in the capacitor.

In each of the TFTs 43, a gate electrode (not shown) is connected to a scan line 44. A source electrode (not shown) is connected to a signal line 46. A drain electrode (not shown) is connected to the photodiode 42. The scan lines 44 and the signal lines 46 are arranged in a lattice-like structure. The number of the scan lines 44 equals to the number "n" of the rows (n rows) of the pixels 37 in the imaging area 38. The number of the signal lines 46 equals to the number "m" of the columns (m columns) of the pixels 37 in the imaging area 38. The scan lines 44 are connected to the gate driver 39. The signal lines 46 are connected to the signal processing circuit 40.

The gate driver 39 activates the TFT 43 and allows the TFT 43 to perform an accumulation operation, a read-out operation (performed after the X-ray irradiation), a reset operation (with no X-ray irradiation), and an irradiation detection operation. In the accumulation operation, the signal charge is accumulated in each of the pixels 37 in accordance with the amount of the X-rays incident thereon. In the read-out operation, the signal charge is read out from the pixels 37. In the irradiation detection operation, the start of the X-ray irradiation is detected. An operation switching section 41a (see also FIG. 5) of the control circuit 41 controls the start timing, of each of the above-described operations performed by the gate driver 39, based on the control signal sent from the imaging control device 23 through a communication section 52.

Figure 3:
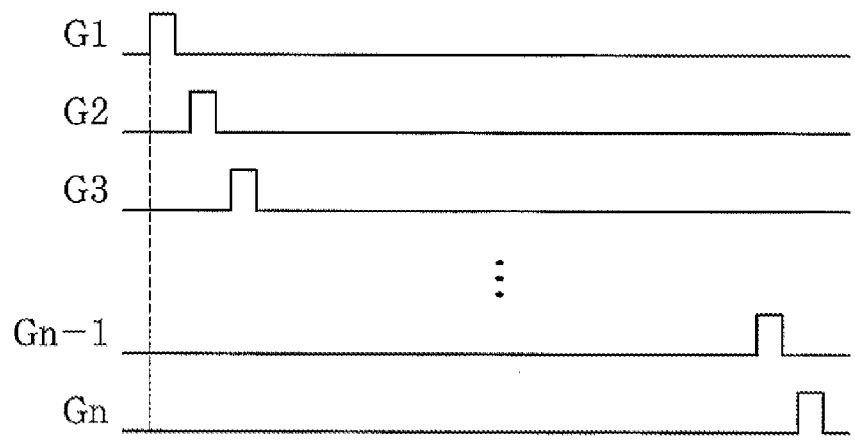
FIG. 3 is a timing chart showing on/off states of a gate pulse during a reset operation and a read-out operation.

In the accumulation operation, the signal charge is accumulated in the pixels 37 while the TFTs are turned off. In the read-out operation, as shown in FIG. 3, the gate driver 39 sequentially generates gate pulses G1 to Gn to activate the respective scan lines 44 on a row-by-row basis. Each of the gate pulses G1 to Gn turns on the TFTs 43 of the corresponding row at a time. When the TFTs 43 are turned on, the electric charge accumulated in the capacitors of the pixels 37 is read out and inputted to the signal processing circuit 40 through the signal lines 46.

Dark charge occurs in the semiconductor layer of the photodiode 42 regardless of presence or absence of the X-rays. The dark charge is accumulated in the capacitor due to the application of the bias voltage. The dark charge occurring in the pixel 37 is a noise component in the image data, so the reset operation is performed to remove the dark charge. The reset operation refers to releasing the dark charge through the signal line 46.

The reset operation of the pixels 37 is performed in a sequential resetting method, for example. In the sequential resetting method, the pixels 37 are reset on a row-by-row basis. As shown in FIG. 3, in the sequential resetting method, the gate driver 39 generates the gate pulses G1 to Gn sequentially to the respective scan lines 44, similar to the read-out operation of the signal charge. Thereby, the TFTs 43 of the respective pixels 37 are turned on, on a row-by-row basis. While the TFTs 43 of the single row are turned on, the dark charge flows from the pixels 37 to integrating amplifiers 47 through the signal lines 46, respectively. In the reset operation, unlike the read-out operation, the electric charge accumulated in the capacitor of the integrating amplifier 47 is not read out by a multiplexer (MUX) 48. Instead, a reset pulse RST turns on a reset switch 47a, and thereby the capacitor discharges.

The signal processing circuit 40 is provided with the integrating amplifiers 47, the MUX 48, and an A/D converter 49. The integrating amplifiers 47 are connected to the respective signal lines 46. Each integrating amplifier 47 includes an operational amplifier and a capacitor connected between input and output terminals of the operational amplifier. The signal line 46 is connected to one of the input terminals of the operational amplifier. The other input terminal is connected to ground (GND, not shown). Each of the integrating amplifiers 47 adds up the electric charge inputted from the corresponding signal line 46. The integrating amplifiers 47 convert the electric charge into voltage signals D1 to Dm, respectively. The output terminal of each of the integrating amplifiers 47 (the integrating amplifiers 47 of each column) is connected to the MUX 48 via an amplifier and a sample hold section (both not shown). The output side of the MUX 48 is connected to the A/D converter 49.

Out of the parallel-connected integrating amplifiers 47, the MUX 48 selects one integrating amplifier 47 at a time, sequentially. The MUX 48 serially inputs the voltage signals D1 to Dm, outputted from the respective integrating amplifiers 47, into the A/D converter 49. The A/D converter 49 converts the voltage signals D1 to Dm into digital data and outputs the digital data to a memory 51. The memory 51 is incorporated in the housing of the electronic cassette 21.

When the MUX 48 reads out the voltage signals (D1 to Dm) of one row from the integrating amplifier 47, the control circuit 41 outputs the reset pulse RST to the integrating amplifier 47. Thereby, the reset switch 47a of the integrating amplifier 47 is turned on to reset the signal charge of one row accumulated in the integrating amplifier 47. Then, the gate driver 39 outputs the gate pulse for the next row to allow the readout of the signal charge of the pixels 37 of the next row. The above operations are repeated sequentially to read out the signal charge of the pixels 37 of all the rows. Note that this reset operation of the integrating amplifiers 47 differs from that of the pixels 37.

Thereafter, image data representing an X-ray image of one frame is stored in the memory 51. The image data is read out from the memory 51 and outputted to the imaging control device 23 via the communication section 52 and a communication cable 26 (see FIG. 1). Thus, the X-ray image of the patient H is obtained.

Figure 4:
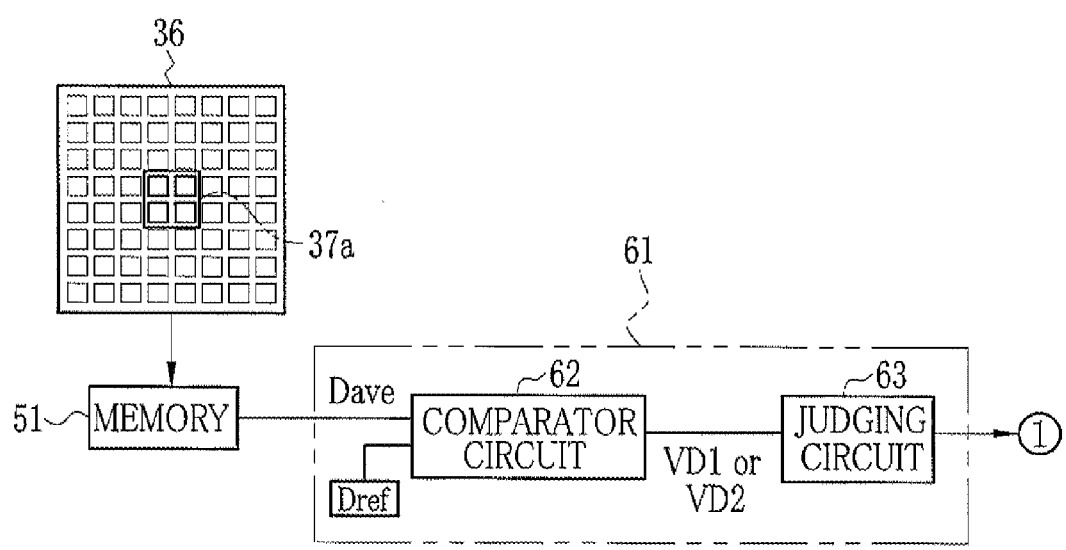
FIG. 4 is a schematic view of an irradiation detecting section for detecting a start of X-ray irradiation.

In an irradiation detection operation, the time of the accumulation operation is set much shorter than the maximum X-ray irradiation time, but long enough to detect the X-ray irradiation. In the irradiation detection operation, the accumulation operation and the read-out operation are repeated alternately for the predetermined number of times. In FIG. 4, in the irradiation detection operation, at least one of the pixels 37 is used as a detection pixel 37a being an irradiation sensor. An irradiation detecting section 61 detects or judges the start of the X-ray irradiation from the X-ray source 13.

In this embodiment, two or more pixels 37 located at or close to the center of the imaging area 38 are used as the detection pixels 37a by way of example. The center or an area close to the center of the imaging area 38 is always within an area (irradiation area) irradiated with the X-rays even if the irradiation area is set smaller than the imaging area 38 according to the size of a region of interest. Thereby, the start of the X-ray irradiation is surely detected regardless of the size of the irradiation area.

The irradiation detecting section 61 includes a comparator circuit 62 and a judging circuit 63. The comparator circuit 62 has two input terminals and an output terminal. To one of the input terminals of the comparator circuit 62, an average value (hereinafter may referred to as the average voltage signal) "Dave" of digital voltage signals from the detection pixels 37a is inputted. To the other input terminal, an irradiation detection threshold value (second threshold value) "Dref" is inputted. The output terminal is connected to the judging circuit 63. The comparator circuit 62 compares the average voltage signal Dave with the irradiation detection threshold value Dref. The comparator circuit 62 outputs a voltage value VD1 from the output terminal when the average voltage signal Dave is less than the irradiation detection threshold value Dref. The comparator circuit 62 outputs a voltage value VD2 from the output terminal when the average voltage signal Dave is greater than or equal to the irradiation detection threshold value Dref. The voltage values VD1 and VD2 are different from each other.

The judging circuit 63 monitors the voltage value outputted from the output terminal of the comparator circuit 62. The judging circuit 63 judges that the X-ray irradiation from the X-ray source 13 is started when the voltage value changes from the VD1 to the VD2, namely, when the average voltage signal Dave is greater than or equal to the irradiation detection threshold value Dref. Thereby, the judging circuit 63 outputs an irradiation detection signal (second signal) indicating the start of the X-ray irradiation, to the operation switching section 41a of the control circuit 41.

When the X-rays are not applied, only the dark charge is accumulated in the pixels 37. In this case, the average voltage signal Dave of the detection pixels 37a, inputted to the comparator circuit 62, is lower than the irradiation detection threshold value Dref. On the other hand, when the X-rays are applied, the signal charge corresponding to the applied X-rays is accumulated in the pixels 37. The value of the signal charge is significantly higher than the value of the dark charge. Accordingly, immediately after the X-ray irradiation, the average voltage signal Dave is greater than or equal to the irradiation detection threshold value Dref. The irradiation detecting section 61 monitors the change in the average voltage signal Dave, occurring subsequent to the X-ray irradiation, to judge the start of the X-ray irradiation. The irradiation detection threshold value Dref is set to a value greater than that of a voltage signal based on the dark charge accumulated by the accumulation operation of the irradiation detection operation.

The acceleration sensor 25 detects acceleration of the electronic cassette 21 in X and Y directions (see FIG. 2) parallel to a plane of the imaging area 38, and in Z direction (not shown) vertical to the X and Y directions, and rotary acceleration about each of X, Y and Z axis, for example. The acceleration sensor 25 outputs the detection results to a shake calculating section 41b (see also FIG. 5) of the control circuit 41. The acceleration sensor 25 starts its operation when the FPD 36 is in the irradiation detection operation. The acceleration sensor 25 stops the operation when the irradiation detection operation ends.

The shake calculating section 41b of the control circuit 41 calculates magnitude (instantaneous value) of a moving vector of the electronic cassette 21 based on the acceleration in the X, Y, and Z directions and rotary acceleration about each of X, Y and Z axis detected by the acceleration sensor 25 using a known method described in Japanese Patent Laid-Open Publication No. 2009-034428, for example. The magnitude of the moving vector represents the magnitude (hereinafter referred to as the shake magnitude) "A" of the shake of the electronic cassette 21 caused by physical shock or impact. A sampling time interval of the shake calculating section 41b for sampling the shake magnitude "A" is sufficiently shorter than the time required to perform one set of the accumulation operation and the read-out operation of the irradiation detection operation.

Figure 5:
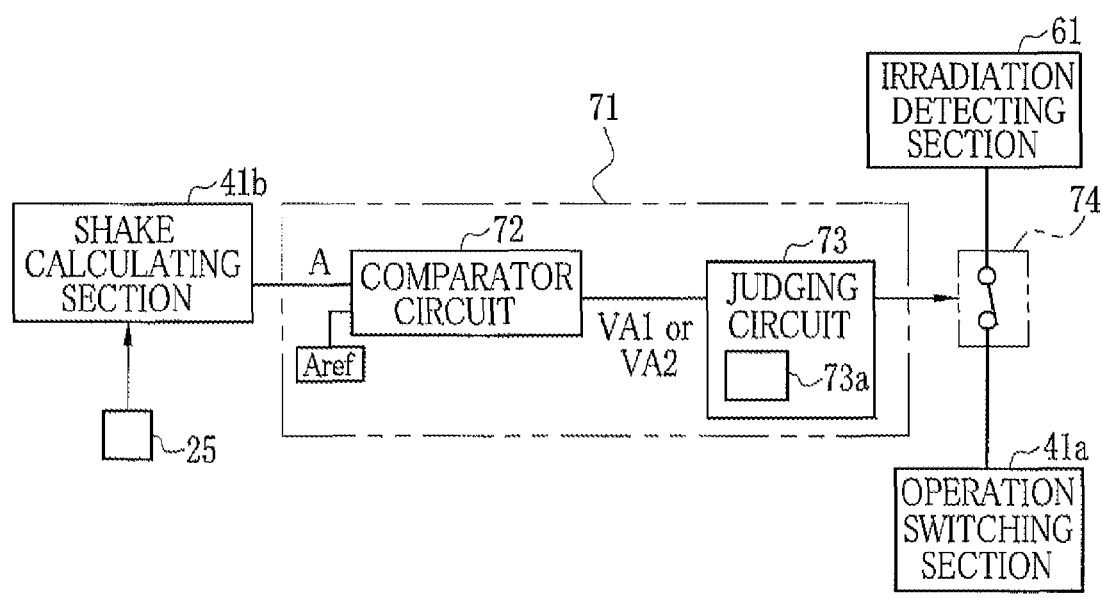
FIG. 5 is a schematic view of a shake detecting section for detecting a shake of an electronic cassette.

The control circuit 41 enables or disables irradiation detection function, that is, the function to detect the start of the X-ray irradiation, of the irradiation detecting section 61 based on the shake magnitude "A" of the electronic cassette 21. To be more specific, as shown in FIG. 5, a shake detecting section (noise detecting section) 71 and a switching element 74 are provided. The shake detecting section 71 includes a comparator circuit 72 and a judging circuit 73. The comparator circuit 72 compares the shake magnitude "A" with a shake detection threshold value (first threshold value) Aref. The switching element 74 is provided between the operation switching section 41a and the irradiation detecting section 61.

The shake detecting section 71 has a configuration similar to or the same as that of the irradiation detecting section 61. The comparator circuit 72 outputs the voltage value VA1 when the shake magnitude "A" is less than the threshold value Aref. The comparator circuit 72 outputs the voltage value VA2 when the shake magnitude "A" is greater than or equal to the threshold value Aref. The judging circuit 73 outputs an ON signal to the switching element 74 when the voltage value is VA1. Thereby, the switching element 74 turns on to connect the irradiation detecting section 61 to the operation switching section 41a.

On the other hand, when the voltage value is changed from the VA1 to the VA2, namely, when the shake magnitude "A" is greater than or equal to the threshold value Aref, the judging circuit 73 outputs an OFF signal (first signal) to the switching element 74. Thereby, the switching element 74 turns off to disconnect the irradiation detecting section 61 from the operation switching section 41a. The judging circuit 73 incorporates a timer 73a. The timer 73a counts the time elapsed from the start of the output of the OFF signal. When the timer 73a counts the predetermined time "T" (see FIG. 7), the judging circuit 73 stops outputting the OFF signal and outputs the ON signal instead. Thereby, the irradiation detecting section 61 restores the connection to the operation switching section 41a.

There are various circumstances where the electronic cassette 21 shakes during the irradiation detection operation. For example, a radiological technologist or the patient H may bump into the support 22 inadvertently. The impact causes the electronic cassette 21 to shake. Additionally, the electronic cassette 21 may shake when the patient H supports the electronic cassette 21 or the electronic cassette 21 is placed on the patient H to perform the X-ray imaging, and when the X-ray imaging is performed in a medical examination car which sways due to the patients getting on and off the car, and when the X-ray imaging is performed using a generator as a battery outside a clinic or hospital, for example.

As is well known, when the electronic cassette 21 shakes, noise caused by the shake is added to the voltage signal of the signal processing circuit 40. Thereby, the value of the average voltage signal Dave, outputted during the irradiation detection operation, increases by the value of the noise component. The noise component may be large enough to make the average voltage signal Dave greater than or equal to the irradiation detection threshold value Dref. This causes the irradiation detecting section 61 to detect the X-ray irradiation erroneously even though the X-ray irradiation has not been started actually.

In this embodiment, vibration noise is detected indirectly from the shake or vibration of the electronic cassette 21. For example, when the shake magnitude "A" is greater than or equal to the threshold value Aref, the switching element 74 is turned off to disconnect the irradiation detecting section 61 from the operation switching section 41a. Namely, the irradiation detection function of the irradiation detecting section 61 is temporarily disabled. Thereby, even if the noise component caused by the shake is added to the average voltage signal Dave such that the average voltage signal Dave is greater than or equal to the irradiation detection threshold value Dref, and the judging circuit 63 of the irradiation detecting section 61 outputs the irradiation detection signal, the irradiation detection signal is not inputted to the operation switching section 41*a*. Accordingly, the electronic cassette 21 does not start the accumulation operation erroneously after the false detection of the X-ray irradiation. Instead, the electronic cassette 21 continues the irradiation detection operation. Thus, the irradiation detection signal is only inputted to the operation switching section 41*a* when the X-ray irradiation is actually started. Thereby, the electronic cassette 21 starts the accumulation operation.

For example, the shake detection threshold value Aref has the magnitude of the shake which causes the noise component substantially equal to the voltage signal corresponding to the irradiation detection threshold value Dref. The time T, after which the OFF signal to the switching element 74 is switched to the ON signal, is set short enough (for example, several msec to 1 sec) so as not to miss the X-ray irradiation started immediately after the shake. The shake, however, does not disappear immediately, and its magnitude decreases with time. Accordingly, it is preferable that the time T includes sufficient allowance for preventing the noise component from being added to the voltage signal when the shake with the magnitude greater than or equal to the threshold value Aref occurs.

After the power of the electronic cassette 21 is turned on, the operation switching section 41*a* causes the FPD 36 to perform the reset operation until the imaging conditions are transmitted from the imaging control device 23. When the imaging conditions are transmitted from the imaging control device 23, the operation switching section 41*a* causes the FPD 36 to stop the reset operation and then start the irradiation detection operation. During the irradiation detection operation, when the operation switching section 41*a* receives the irradiation detection signal from the irradiation detecting section 61, the operation switching section 41*a* causes the FPD 36 to stop the irradiation detection operation and then start the accumulation operation. Here, before the start of the accumulation operation, the operation switching section 41*a* causes the FPD 36 to perform the reset operation once. With the use of the timer, the operation switching section 41*a* counts the time elapsed from the start of the accumulation operation. When the timer counts the predetermined time set by the imaging conditions, the operation switching section 41*a* causes the FPD 36 to stop the accumulation operation and then start the read-out operation.

The imaging control device 23 is connected in a communicable manner to the electronic cassette 21, wirelessly or via the communication cable 26, to control the electronic cassette 21. To be more specific, the imaging control device 23 transmits the imaging conditions to the electronic cassette 21 to set signal processing conditions (for example, the gain of the amplifier) of the FPD 36 and controls the operations of the FPD 36 indirectly. The imaging control device 23 transmits the image data from the electronic cassette 21 to the console 24.

In FIG. 1, the imaging control device 23 has a CPU 23*a*, a communication section 23*b*, and a memory 23*c*. The CPU 23*a* controls overall operation of the imaging control device 23. The communication section 23*b* communicates with the electronic cassette 21 wirelessly or via the communication cable 26. The communication section 23*b* communicates with the console 24 via a communication cable 27. The communication section 23*b* and the memory 23*c* are connected to the CPU 23*a*. The memory 23*c* stores a control program to be executed by the CPU 23*a* and various pieces of information such as the irradiation detection threshold value Dref and the shake detection threshold value Aref. The irradiation detection threshold value Dref and the shake detection threshold value Aref, stored in the memory 23*c*, are transmitted to the electronic cassette 21 via the communication cable 26 after the power of the electronic cassette 21 is turned on. The irradiation detection threshold value Dref is inputted to the comparator circuit 62. The shake detection threshold value Aref is inputted to the comparator circuit 72.

The console 24 is connected to the imaging control device 23 via the communication cable 27. The console 24 transmits the imaging conditions to the imaging control device 23. The console 24 performs various processes such as offset correction and gain correction to the data of the X-ray image transmitted from the imaging control device 23. Then, the X-ray image is displayed on the display of the console 24. The data of the X-ray image is stored in a data storage device, for example, a hard disk or a memory (not shown) in the console 24, or an image storage server (not shown) connected to the console 24 through a network.

The console 24 receives an examination request which includes patient information, for example, the patient's name, gender, age, a region of interest, and a purpose of the examination, and displays the examination request on the display. The examination request may be inputted from an external system, for example, HIS (Hospital Information System) or RIS (Radiology Information System) that manages patient information and examination information of the radiation examination. Alternatively, the examination request may be inputted manually. The radiological technologist confirms the details of the examination request on the display and inputs the imaging conditions suitable for the examination request through an operation screen of the console 24.

Hereinafter, an operation of the above configuration is described with reference to timing charts in FIGS. 6 and 7, and a flowchart in FIG. 8. The numerals and letters (for example, S10) are common to FIGS. 6, 7, and 8.

To perform imaging using the X-ray imaging system 10, first, the electronic cassette 21 attached to the support 22 is adjusted to a level or vertical position appropriate for the region of interest of the patient H. The level of the X-ray source 13 and the size of the X-ray field are adjusted in accordance with the level of the electronic cassette 21 and the size of the region of interest.

Next, as shown in a step 10 (S10) in FIG. 8, the power of the electronic cassette 21 is turned on. Thereby, the bias voltage is supplied from the power circuit to the pixels 37 of the PFD 36, and the gate driver 39 and the signal processing circuit 40 are activated. Thus, the operation switching section 41*a* causes the FPD 36 to start the reset operation of all the pixels 37 (S11). Then, the imaging conditions are inputted from the console 24. The imaging conditions inputted are set to the electronic cassette 21 through the imaging control device 23. The imaging conditions inputted are also set to the source control device 14. Upon receipt of the imaging conditions from the imaging control device 23 (YES in S12), the operation switching section 41*a* causes the FPD 36 to stop the reset operation and start the irradiation detection operation (S13).

When the above imaging preparation is completed, the irradiation switch 15 is pressed one step. Thereby, the warm-up start signal is transmitted to the source control device 14 to start the warm-up of the X-ray source 13. After the warm-up, the irradiation switch 15 is pressed two steps down to transmit the irradiation start signal to the source control device 14. Thereby, the X-ray irradiation is started.

During the irradiation detection operation, first, the presence of the shake of the electronic cassette 21 is checked. When the shake is not detected (NO in S14), whether the X-ray irradiation is started is detected. To detect the start of the X-ray irradiation, as shown in FIG. 4, signal charge of each of the four detection pixels 37*a* is readout and written as a voltage value on the memory 51. Next, the four voltage values are read out from the memory 51 to obtain an average value Dave of the four voltage values. The comparator circuit 62 compares the average value Dave with the irradiation detection threshold value Dref. When the average value Dave is less than the irradiation detection threshold value Dref, the judging circuit 63 judges that the X-ray irradiation is not started (NO in S15).

While the shake is not detected, the accumulation operation and the read-out operation of the detection pixels 37*a* are performed alternately and repeatedly. If the start of the X-ray irradiation is not detected during the N (N is an integer) times of the accumulation operations and the N times of the read-out operations (YES in S21), the irradiation detection operation returns to the S11. The operation switching section 41*a* performs the reset operation of all the pixels 37 in the FPD 36.

When the average value Dave is greater than or equal to the threshold value Dref, the judging circuit 63 judges that the X-ray irradiation is started (YES in S15). Thereby, the operation switching section 41*a* causes the FPD 36 to perform the reset operation once (illustrations are omitted in FIGS. 6 and 8). Then, the TFTs 43 of all the pixels 37 are turned off and the operation switching section 41*a* causes the FPD 36 to start the accumulation operation (S16). During the accumulation operation, the X-rays passed through the patient H are incident on the imaging area 38 of the FPD 36. In each of the pixels 37, the signal charge corresponding to the amount of the X-rays incident on the pixel 37 is accumulated.

The source control device 14 stops the X-ray irradiation when the X-ray irradiation time set by the imaging conditions elapses. The FPD 36 also stops the accumulation operation when the predetermined time corresponding to the X-ray irradiation time elapses (YES in S17), and starts the read-out operation (S18). In the read-out operation, the signal charge accumulated in the pixels 37 is read out sequentially on a row-by-row basis, and stored as the X-ray image data of one frame in the memory 51. The X-ray image data is transmitted to the console 24 through the imaging control device 23. Thereby, the X-ray image detection is completed. For the subsequent X-ray imaging, when the next imaging conditions are not set, the FPD 36 returns to the reset operation, that is, the state immediately after turning on of the power. When the next imaging conditions are set, the FPD 36 returns to the S13 and performs the irradiation detection operation again.

During the irradiation detection operation, when the electronic cassette 21 shakes or vibrates, the shake calculating section 41*b* calculates the shake magnitude "A" from a signal from the acceleration sensor 25. The comparator circuit 72 of the shake detecting section 71 compares the shake magnitude A with the threshold value Aref.

As shown in a lower portion of FIG. 6, when the electronic cassette 21 shakes during the irradiation detection operation, and the shake magnitude "A" is lower than the threshold value Aref (NO in S14), the irradiation detection function of the irradiation detecting section 61 is kept enabled to continue the irradiation detection operation. Conversely, as shown in a lower portion of FIG. 7, when the shake magnitude "A" is greater than or equal to the threshold value Aref, and when the judging circuit 73 detects that the output of the comparator circuit 72 is changed to the value VA2 (YES in S14), the judging circuit 73 transmits the OFF signal to the switching element 74 that connects the operation switching section 41*a* and the irradiation detecting section 61. Thereby, the switching element 74 is turned off. Namely, the operation switching section 41*a* and the irradiation detecting section 61 are disconnected and thus the irradiation detection function of the irradiation detecting section 61 is disabled (S19).

When the predetermined time T elapses after the transmission of the OFF signal to the switching element 74 (YES in S20), the judging circuit 73 transmits the ON signal to the switching element 74 to turn on the switching element 74. Thereby, the operation switching section 41*a* and the irradiation detecting section 61 restore the connection, and thus the irradiation detection function of the irradiation detecting section 61 is enabled. Accordingly, the detection by the irradiation detecting section 61 is resumed as described above. In this example, the shake magnitude "A" reaches or exceeds the threshold value Aref just once during the irradiation detection operation. Actually, this may happen two or more times during the irradiation detection operation. If so, the irradiation detection function is disabled every time the shake magnitude A reaches or exceeds the threshold value Aref.

As described above, in the present invention, the false detection of the start of the X-ray irradiation is surely prevented because the irradiation detection function is disabled in accordance with the magnitude of the shake of the electronic cassette 21. Accordingly, unnecessary operations of the electronic cassette 21 caused by the false detection are prevented, which no longer hinder the image capture timing. As a result, the X-ray imaging is performed with high efficiency and less electricity.

In the above embodiment, the switching element 74, arranged between the operation switching section 41*a* and the irradiation detecting section 61, is turned off to disable the irradiation detection function. Alternatively, the control circuit 41 may disable the irradiation detection function. For example, the control circuit 41 may cause the operation switching section 41*a* not to receive the irradiation detection signal from the irradiation detecting section 61 while the judging circuit 73 of the shake detecting section 71 outputs a signal corresponding to the OFF signal of the above embodiment. Alternatively, when the shake magnitude "A" is greater than or equal to the shake detection threshold value Aref, a voltage signal less than the irradiation detection threshold value Dref is inputted to one of the input terminals of the comparator circuit 62 of the irradiation detecting section 61. To the other input terminal, the irradiation detection threshold value Dref is inputted. Thereby, the comparator circuit 62 keeps outputting the signal value VD1, prohibiting the judging circuit 63 to output the irradiation detection signal. Alternatively, the power supply to the irradiation detecting section 61 may be stopped to disable the operation of the irradiation detecting section 61 itself.

In the above embodiment, the irradiation detection function is disabled until the predetermined time T elapses after the shake magnitude "A" is greater than or equal to the threshold value Aref. Alternatively, the irradiation detection function may be disabled while the shake magnitude "A" is greater than or equal to the threshold value Aref.

The X-ray imaging system 10 is not limited to the stationary type installed in a radiography room at a hospital. Alternatively, the X-ray imaging system 10 may be installed in an medical examination car. The X-ray source 13, the source control device 14, the electronic cassette 21, the imaging control device 23 and the like may be applied to a portable system for use in the X-ray imaging on-site, for example, in an accident or disaster scene where emergency medical care is necessary or at a patient's house to perform home care. Specifically, in the X-ray imaging system installed in the medical examination car and the portable X-ray imaging system, the electronic cassette 21 is more frequently exposed to physical shock than that in the stationary-type system installed in the radiography room. Accordingly, the present invention is especially effective when applied to the X-ray imaging system installed in the medical examination car and the portable X-ray imaging system.

Unlike unexpected physical shock, vibration caused by the generator, for use in the X-ray imaging outside the hospital, is substantially constant and continuous. When the magnitude of such vibration is greater than or equal to the threshold value Aref, the irradiation detection function is disabled continuously. To prevent this, it is preferable to calculate the magnitude of the vibration caused by the generator before the image capture, in a state that the vibration other than that caused by the generator is eliminated from the electronic cassette 21. Then, the magnitude of vibration caused by the generator is added to the shake detection threshold value Aref to increase the threshold value Aref.

In the above embodiment, a part of the pixels 37 are used as the detection pixels 37a to detect the start of the X-ray irradiation by way of example. Separately from the pixels 37, an irradiation detection sensor may be installed to the electronic cassette 21. The present invention is especially effective when the irradiation detection sensor is susceptible to noise caused by vibration or shake, and when a noise component occurs with a little shake. In this case, after the power of the electronic cassette 21 is turned on, only the bias voltage is applied to each pixel 37 and no other operation is performed thereto. Upon receipt of the imaging conditions, the reset operation is performed. When the start of the X-ray irradiation is detected by the irradiation detection sensor, the reset operation is stopped and then the accumulation operation of the pixels 37 is performed as in the above embodiment. Thus, timing of changing the operations of the FPD 36 is not limited to the above embodiment and can be changed as necessary.

Instead of or in addition to the acceleration sensor 25, a pressure sensor may be used as a means for indirectly detecting the noise caused by vibration or shake. A change in pressure (for example, strain) on the housing of the electronic cassette 21 caused by the impact thereon is detected using the pressure sensor. The irradiation detection function is enabled or disabled in accordance with the magnitude of a pressure value.

In the above embodiment, the X-ray irradiation is detected by the comparison between the digital voltage signal that has been subjected to the A/D conversion and the threshold value. Alternatively or in addition, the X-ray irradiation may be detected by the comparison between an analog voltage signal outputted from the integrating amplifier 47 and the threshold value.

Noise other than that caused by vibration or shake, for example, noise based on temperature detected by a temperature sensor or radio noise may be detected. The irradiation detection function may be enabled or disabled based on the noise detected.

Instead of the sequential resetting method of the above embodiment, a parallel resetting method or an all-pixel resetting method may be used. In the parallel resetting method, the sequential resetting method is applied to two or more rows of the pixels as a group. The dark charge is discharged from the groups simultaneously in parallel. In the all resetting method, a gate pulse is inputted to every row to discharge the dark charge of all the pixels at a time. The parallel resetting method or the all-pixel resetting method enhances the speed of the reset operation.

Some of the X-ray sources do not require the warm-up, for example, a stationary anode type and a cold cathode type that does not require preheating. In this case, the irradiation switch may only have a function to issue the radiation start signal. Even if the X-ray source needs the warm-up, it may be unnecessary to provide the irradiation switch with the function to issue the warm-up start signal. For example, when the irradiation switch inputs the irradiation start signal to the source control device, the source control device allows the X-ray source to start the warm-up responsive to the irradiation start signal, and then allows the X-ray source to start the irradiation after the warm-up.

In the above embodiment, the electronic cassette 21 is provided separately from the imaging control device 23 by way of example. Alternatively, the electronic cassette and the imaging control device may be formed integrally. For example, the function of the imaging control device 23 may be incorporated into the control circuit 41. In the above embodiment, the console 24 performs the image processing. Alternatively, the imaging control device 23 may perform the image processing.

In the above embodiment, the electronic cassette, being the portable X-ray image detection device, is described by way of example. The present invention is also applicable to the stationary X-ray image detection devices.

The present invention is not limited the X-rays. The present invention is also applicable to imaging systems using radiation other than the X-rays, for example gamma rays.

Various changes and modifications are possible in the present invention and may be understood to be within the present invention.

What is claimed is:

1. A radiation image detection device comprising:
a radiation image detector having a plurality of pixels arranged thereon, the radiation image detector performing accumulation operation, each pixel detecting radiation emitted from a radiation source to accumulate signal charge in the accumulation operation;
an irradiation sensor for detecting the radiation;
an irradiation detecting section for detecting a start of irradiation of the radiation based on a signal from the irradiation sensor;
a noise sensor; and
a control section for enabling or disabling the irradiation detecting section based on a signal from the noise sensor, wherein the control section includes a noise detecting section for detecting magnitude of the signal from the noise sensor, and the noise detecting section outputs a first signal to the control section when the magnitude of the signal from the noise sensor is greater than or equal to a first threshold value, and the control section disables the irradiation detecting section when the first signal is inputted from the noise detecting section, and
wherein the irradiation detecting section outputs a second signal to the control section when magnitude of the signal from the irradiation sensor is greater than or equal to a second threshold value, and the second signal represents the start of the irradiation of the radiation, and the control section enables the irradiation detecting section to allow the radiation image detector to perform the accumulation operation when the second signal is inputted to the control section from the irradiation detecting section and the first signal is not inputted to the control section from the noise detecting section.

2. The radiation image detection device of claim 1, wherein the control section disables the irradiation detecting section by disconnecting the control section from the irradiation detecting section.

3. The radiation image detection device of claim 1, wherein the control section disables the irradiation detecting section by controlling the irradiation detecting section not to output the second signal.

4. The radiation image detection device of claim 1, wherein the control section disables the irradiation detecting section by not receiving the second signal even if the second signal is inputted to the control section.

5. The radiation image detection device of claim 1, wherein the control section disables the irradiation detecting section after the first signal is outputted from the noise detecting section.

6. The radiation image detection device of claim 5, wherein the predetermined time is a time necessary for a noise component in the signal from the irradiation sensor to decrease its magnitude to a negligible value.

7. The radiation image detection device of claim 1, wherein the noise sensor is a vibration sensor.

8. The radiation image detection device of claim 7, wherein the vibration sensor is an acceleration sensor.

9. The radiation image detection device of claim 1, wherein the irradiation sensor also serves as the radiation image detector.

10. The radiation image detection device of claim 9, wherein the at least one pixel positioned close to a center of the radiation image detector is used as the irradiation sensor.

11. The radiation image detection device of claim 9, wherein the control section allows the radiation image detector to perform an irradiation detection operation, and the irradiation detection operation includes the accumulation operation and a read-out operation repeated alternately for predetermined number of times, and the signal charge is converted into an electric signal and then the electric signal is outputted in the read-out operation.

12. The radiation image detection device of claim 1, wherein the radiation image detection device is an electronic cassette having the radiation image detector enclosed in a portable housing.

13. A method for controlling a radiation image detection device comprising the steps of:
    detecting occurrence of a cause of noise based on a first signal from a noise sensor; and
    disabling an irradiation detecting section when the first signal is greater than or equal to a first threshold value, the irradiation detecting section judging a start of irradiation of radiation based on a detection result of an irradiation sensor,
    wherein the irradiation detecting section outputs a second signal when a magnitude of a signal from the irradiation sensor is greater than or equal to a second threshold value, and the second signal represents the start of irradiation of radiation, said method further comprising enabling the irradiation detecting section to allow a radiation image detector to perform an accumulation operation when the second signal is output from the irradiation detecting section and the first signal is not output from the noise sensor.

* * * * *